United States Patent [19]

Neuzil

[11] Patent Number: 4,482,777
[45] Date of Patent: Nov. 13, 1984

[54] SEPARATION OF ORTHO BI-ALKYL SUBSTITUTED MONOCYCLIC AROMATIC ISOMERS

[75] Inventor: Richard W. Neuzil, Downers Grove, Ill.

[73] Assignee: UOP Inc., Des Plaines, Ill.

[21] Appl. No.: 596,212

[22] Filed: Apr. 2, 1984

[51] Int. Cl.³ .............................................. C07C 7/12
[52] U.S. Cl. ................................. 585/828; 208/310 Z
[58] Field of Search ...................... 208/310 Z; 585/828, 585/827, 826

[56] References Cited

U.S. PATENT DOCUMENTS

| | | | |
|---|---|---|---|
| B 426,274 | 1/1976 | Hedge | 260/674 SA |
| 2,985,589 | 5/1961 | Broughton et al. | 210/34 |
| 3,201,491 | 8/1965 | Stine et al. | 260/676 |
| 3,374,182 | 3/1968 | Young | 252/455 |
| 3,558,730 | 1/1971 | Neuzil | 585/328 |
| 3,558,732 | 1/1971 | Neuzil | 208/310 Z X |
| 3,626,020 | 12/1971 | Neuzil | 260/674 SA |
| 3,663,638 | 5/1972 | Neuzil | 260/674 SA |
| 3,665,046 | 5/1972 | De Rosset | 260/674 SA |
| 3,668,266 | 6/1972 | Chen et al. | 260/674 |
| 3,686,342 | 8/1972 | Neuzil | 585/828 |
| 3,686,343 | 8/1972 | Beardon, Jr. et al. | 260/674 SA |
| 3,700,744 | 10/1972 | Berger et al. | 260/668 A |
| 3,734,974 | 5/1973 | Neuzil | 260/674 SA |
| 3,894,109 | 7/1975 | Rosback | 260/674 SA |
| 3,917,734 | 11/1975 | De Rosset | 208/310 Z X |
| 3,943,182 | 3/1976 | Neuzil et al. | 208/310 Z X |
| 3,943,184 | 3/1976 | Rosback | 208/310 Z |
| 3,997,619 | 12/1976 | Neuzil | 208/310 Z |
| 3,997,620 | 12/1976 | Neuzil | 260/674 SA |
| 4,021,499 | 5/1977 | Bieser | 585/828 |
| 4,326,092 | 4/1982 | Neuzil | 585/828 |
| 4,376,226 | 3/1983 | Rosenfeld et al. | 585/828 |
| 4,423,279 | 12/1983 | Kulprathipanja | 585/828 |

*Primary Examiner*—Delbert E. Gantz
*Assistant Examiner*—Glenn A. Caldarola
*Attorney, Agent, or Firm*—William H. Page, II; Louis A. Morris

[57] ABSTRACT

A process for separating the ortho-isomer from a feed mixture comprising at least two bi-alkyl substituted monocyclic aromatic isomers, including the ortho-isomers, the isomers having from 9 to about 18 carbon atoms per molecule. The process comprises contacting, at adsorption conditions, the feed with an adsorbent comprising a crystalline aluminosilicate consisting essentially of a sodium or calcium Y-type zeolite or sodium X-type zeolite which selectively adsorbs the ortho-isomers. The feed is removed from the adsorbent, and the ortho-isomers recovered by desorption at desorption conditions with a desorbent material comprising a $C_8$ or heavier monocyclic aromatic with a boiling point at least 5° C. different than that of the feed mixture when the adsorbent is the sodium Y-type zeolite, or a $C_8$ or lighter monocyclic aromatic when the adsorbent is a sodium X or calcium Y-type zeolite.

The process is particularly amenable to the employment of a simulated moving bed flow scheme.

16 Claims, No Drawings

SEPARATION OF ORTHO BI-ALKYL SUBSTITUTED MONOCYCLIC AROMATIC ISOMERS

BACKGROUND OF THE INVENTION

The field of art to which the claimed invention pertains is hydrocarbon separation. More specifically, the invention relates to a process for separating an ortho-isomer from a feed mixture comprising at least two bi-alkyl substituted monocyclic aromatic isomers, including the ortho-isomer, which process employs a particular zeolitic adsorbent.

BACKGROUND INFORMATION

It is well known in the separation art that certain crystalline aluminosilicates can be used to separate one hydrocarbon type from another hydrocarbon type. The separation of normal paraffins from branched chain paraffins, for example, can be accomplished by using a type A zeolite which has pore openings from 3 to about 5 Angstroms. Such a separation process is disclosed in U.S. Pat. Nos. 2,985,589 to Broughton et al. and 3,201,491 to Stine. These adsorbents allow a separation based on the physical size differences in the molecules by allowing the smaller or normal hydrocarbons to be passed into the cavities within the zeolitic adsorbent, while excluding the larger or branched chain molecules.

In addition to being used in processes for separating hydrocarbon types, adsorbents comprising type X or Y zeolites have also been employed in processes to separate individual hydrocarbon isomers. In the processes described, for example, in U.S. Pat. Nos. 3,626,020 to Neuzil, 3,663,638 to Neuzil, 3,655,046 to de Rosset, 3,668,266 to Chen et al., 3,686,343 to Bearden Jr. et al., 3,700,744 to Berger et al., 3,734,974 to Neuzil, 3,894,109 to Rosback, 3,997,620 to Neuzil and B426,274 to Hedge, particular zeolitic adsorbents are used to separate the para isomer of bi-alkyl substituted monocyclic aromatics from the other isomers, particularly para-xylene from other xylene isomers. It is also known that the adsorptive capacity of certain zeolites for certain separations is improved by contacting the zeolite with an aqueous caustic solution. In U.S. Pat. No. 3,374,182 to Young, for example, zeolites so treated are said to be effective in separating aromatic hydrocarbons from non-aromatic hydrocarbons of the same molecular size.

In U.S. Pat. No. 4,376,226 to Rosenfeld et al. the separation of the ortho aromatic isomer from a mixture of aromatic isomers is disclosed using CSZ-1 as a crystalline aluminosilicate adsorbent and a mon-aromatic hydrocarbon as a desorbent material. CSZ-1 has a composition in terms of mole ratios of oxides of 0.05 to 0.55 cesium and/or thallium: 0.45 to 0.95 $Na_2O:Al_2O_3$:3 to 7 $SiO_2:XH_2O$, where X is 0 to 10. The CSZ-1 must contain cesium and/or thallium. The mono-aromatic desorbents specifically mentioned are toluene, benzene and diethylbenzene.

SUMMARY OF THE INVENTION

In brief summary the present invention is, in one embodiment, a process for separating the ortho-isomer from a feed mixture comprising at least two bi-alkyl substituted monocyclic aromatic isomers, including the ortho-isomer, the isomers having from 9 to about 18 carbon atoms per molecule. The process comprises contacting, at adsorption conditions, the feed with an adsorbent comprising a crystalline aluminosilicate consisting essentially of a sodium or calcium Y-type zeolite or sodium X-type zeolite which selectively adsorbs the ortho-isomer. The feed is removed from the adsorbent, and the ortho-isomer then recovered by desorption at desorption conditions with a desorbent material comprising a $C_8$ or heavier monocyclic aromatic with a boiling point at least 5° C. different than that of the feed mixture when the adsorbent is the sodium Y-type zeolite, or a $C_8$ or lighter monocyclic aromatic when the adsorbent is a sodium X or calcium Y-type zeolite.

Other embodiments of the present invention encompass details about feed mixtures, flow schemes and operating conditions, all of which are hereinafter disclosed in the following discussion of each of the facets of the present invention.

DESCRIPTION OF THE INVENTION

At the outset the definitions of various terms used throughout this specification will be useful in making clear the operation, objects and advantages of the present invention.

A "feed mixture" is a mixture containing one or more extract components and one or more raffinate components to be fed to an adsorbent of our process. The term "feed stream" indicates a stream of feed mixture which passes to an adsorbent used in the process.

An "extract component" is a type of compound or a compound, such as an aromatic isomer, that is more selectively adsorbed by the adsorbent while a "raffinate component" is a compound or type of compound that is less selectively adsorbed. In this process, the ortho-isomer is the extract component and one or more other aromatic isomers is a raffinate component. The term "raffinate stream" or "raffinate output stream" means a stream through which a raffinate component is removed from an adsorbent. The composition of the raffinate stream can vary from essentially 100% desorbent material (hereinafter defined) to essentially 100% raffinate components. The term "extract stream" or "extract output stream" shall mean a stream through which an extract material which has been desorbed by a desorbent material is removed from the adsorbent. The composition of the extract stream, likewise, can vary from essentially 100% desorbent material to essentially 100% extract components. Although it is possible by the process of this invention to produce high-purity extract product (hereinafter defined) or a raffinate product (hereinafter defined) at high recoveries, it will be appreciated that an extract component is never completely adsorbed by the adsorbent, nor is a raffinate component completely non-adsorbed by the adsorbent. Therefore, small amounts of a raffinate component can appear in the extract stream, and, likewise, small amounts of an extract component can appear in the raffinate stream. The extract and raffinate streams then are further distinguished from each other and from the feed mixture by the ratio of the concentrations of an extract component and a specific raffinate component, both appearing in the particular stream. For example, the ratio of concentration of the more selectively adsorbed ortho-isomer to the concentration of less selectively adsorbed para- or meta-isomer will be highest in the extract stream, next highest in the feed mixture, and lowest in the raffinate stream. Likewise, the ratio of the less selectively adsorbed meta- or para-isomers to the more selectively adsorbed ortho-isomer will be highest in the raffinate stream, next highest in the feed mixture, and the lowest in the extract stream. The term "desorbent mixture" shall mean generally a material capable of desorbing an extract component. The term "desorbent stream" or "desorbent input stream" indicates the stream through which desorbent material passes to the adsorbent. When the extract stream and the raffinate stream contain desorbent materials, at least a portion of the extract stream and preferably at least a portion of the raffinate stream from the adsorbent will be passed to separation means, typically fractionators, where at least a portion of desorbent material will be separated at separation conditions to produce an extract product and a raffinate product. The terms "extract product" and "raffinate product" mean products produced by the process containing, respectively, an extract component and a raffinate component in higher concentrations than those found in the respective extract stream and the raffinate stream. The term "selective pore volume" of the adsorbent is defined as the volume of the adsorbent which selectively adsorbs extract components from a feed mixture. The term "non-selective void volume" of an adsorbent is the volume of an adsorbent which does not selectively retain an extract component from a feed mixture. This volume includes the cavities of the adsorbent which contain no adsorptive sites and the interstitial void spaces between adsorbent particles. The selective pore volume and the non-selective void volume are generally expressed in volumetric quantities and are of importance in determining the proper flow rates of fluid required to be passed into the process for efficient operations to take place for a given quantity of adsorbent.

Feed mixtures which can be utilized in the process of this invention will comprise at least two bi-alkyl substituted monocyclic aromatic isomers. These isomers can be characterized by reference to Formula 1 below:

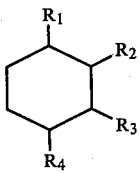

wherein $R_1$, $R_2$, $R_3$ and $R_4$ are selected from the group of alkyl chains and positioned in a manner to provide bi-alkyl substitution at either ortho-, meta-, or para-isomer positions. The R substitutional groups can include alkyl groups ranging from methyl substitution groups up to and including chains having 11 or less carbon atoms per chain. The alkyl side chains can be both normal and branched in nature and are preferably saturated chains.

Thus feed mixtures to this process can contain such specific representative compounds as the various isomers of methylethylbenzene, diethylbenzene, isopropyltoluene (cymene), the methylpropylbenzenes, ethylpropylbenzenes, methylbutylbenzenes, ethylbutylbenzenes, dipropylbenzenes, methylpentylbenzenes, etc., and combinations thereof. The above list only represents a small fraction of compounds whose isomers can be separated by the adsorptive-separation process of this invention. Thus the process of this invention will be used for example to separate ortho-methylethylbenzene from a feed mixture comprising ortho-methylethylbenzene and at least one other methylethylbenzene isomer; ortho-diethylbenzene from a feed mixture comprising ortho-diethylbenzene and at least one other diethylbenzene isomer; and ortho-cymene from a feed mixture comprising ortho-cymene and at least one other cymene isomer to name a few. The most likely separations for employment of the present invention, however, is the separation of ortho-ethyltoluene from other ethyltoluene isomers or ortho-diethylbenzene from other diethylbenzene isomers.

The isomers of such compounds are separated by this adsorbent according to their configuration depending whether they are of a para-, meta-, or ortho-isomer construction. Specifically, the ortho-isomer is selectively adsorbed relative to the other isomers. It is contemplated that when feed mixtures contain more than one homolog of isomers (for example, $C_9$ isomers in mixture with $C_{10}$ or $C_{11}$ isomers) molecular weight differences may unduly interfere with selective adsorption based upon isomer configuration differences. It is therefore preferred that feed mixtures to be separated by this process contain only a single class of aromatic isomers, that is, aromatic isomers having an equal number of carbon atoms per molecule. It is preferable that the isomers have as their only differences the location of the alkyl substituted groups in a para-, meta-, or ortho-position. The alkyl structures should preferably be the same for each isomer of a class. In some instances an isomer may have alkyl chains which are both normal or branched or one branched and one normal.

The feed mixtures may contain small quantities of straight or branched chain paraffins, cycloparaffins, or olefinic material. It is preferable to have these quantities at a minimum amount in order to prevent contamination of products from this process by materials which are not selectively adsorbed or separated by the adsorbent. Preferably the above-mentioned contaminants should be less than about 20% of the volume of the feed mixture passed into the process.

To separate the ortho-isomer from a feed mixture containing ortho-isomer and at least one other aromatic isomer, the mixture is contacted with the adsorbent and the ortho-isomer is more selectively adsorbed and retained by the adsorbent while the other isomers are relatively unadsorbed and are removed from the interstitial void spaces between the particles of adsorbent and the surface of the adsorbent. The adsorbent containing the more selectively adsorbed ortho-isomer is referred to as a "rich" adsorbent—rich in the more selectively adsorbed ortho-isomer. The ortho-isomer is then recovered from the rich adsorbent by contacting the rich adsorbent with a desorbent material.

The term "desorbent material" as used herein shall mean any fluid substance capable of removing a selectively adsorbed feed component from the adsorbent. Generally, in a swing-bed system in which the selectively adsorbed feed component is removed from the adsorbent by a purge stream, desorbent material selection is not too critical and desorbent materials comprising gaseous hydrocarbons such as methane, ethane, etc., or other types of gases such as nitrogen or hydrogen may be used at elevated temperatures or reduced pressures or both to effectively purge the adsorbed feed component from the adsorbent. However, in adsorptive separation processes which employ zeolitic adsorbents and which are generally operated continuously at substantially constant pressures and temperatures to insure liquid phase, the desorbent material relied upon must be judiciously selected to satisfy several criteria. First, the desorbent material must displace the extract components from the adsorbent with reasonable mass flow rates without itself being so strongly adsorbed as to unduly prevent the extract component from displacing the desorbent material in a following adsorption cycle. Expressed in terms of the selectivity (hereinafter discussed in more detail), it is preferred that the adsorbent be more selective for the extract component with respect to a raffinate component than it is for the desorbent material with respect to a raffinate component. Secondly, desorbent materials must be compatible with the particular adsorbent and the particular feed mixture. More specifically, they must not reduce or destroy the critical selectivity of the adsorbent for the extract components with respect to the raffinate component. Desorbent materials to be used in the process of this invention should additionally be substances which are easily separable from the feed mixture that is passed into the process. After desorbing the extract components of the feed, both desorbent material and the extract components are typically removed in admixture from the adsorbent. Likewise, one or more raffinate components is typically withdrawn from the adsorbent in admixture with desorbent material and without a method of separating at least a portion of desorbent material, such as distillation, neither the purity of the extract product nor the purity of the raffinate product would be very high. It is therefore contemplated that any desorbent material used in this process will have a substantially different average boiling point than that of the feed mixture to allow separation of desorbent material from feed components in the extract and raffinate streams by simple fractionation thereby permitting reuse of desorbent material in the process. The term "substantially different" as used herein shall mean that the difference between the average boiling points between the desorbent material and the feed mixture shall be at least about 5° C. The boiling range of the desorbent material may be higher or lower than that of the feed mixture.

In the preferred isothermal, isobaric, liquid-phase operation of the process of this invention, it has been found that the effective desorbent materials comprise the $C_8$ or heavier monocyclic aromatics when the adsorbent is a Y-type zeolite, or a $C_8$ or lighter monocyclic aromatic when the adsorbent is a sodium X or calcium Y-type zeolite. This is in contradistinction to the aforementioned U.S. Pat. No. 4,376,226 to Rosenfeld et al. which specifically discloses toluene, benzene and diethylbenzene for use as desorbents with the same zeolitic adsorbent.

The prior art has recognized that certain characteristics of adsorbents are highly desirable, if not absolutely necessary, to the successful operation of a selective adsorption process. Among such characteristics are: adsorptive capacity for some volume of an extract component per volume of adsorbent; the selective adsorption of an extract component with respect to a raffinate component and the desorbent material; and, sufficiently fast rates of adsorption and desorption of the extract components to and from the adsorbent.

Capacity of the adsorbent for adsorbing a specific volume of one or more extract component is, of course, a necessity; without such capacity the adsorbent is useless for adsorptive separation. Furthermore, the higher the adsorbent's capacity for an extract component the better is the adsorbent. Increased capacity of a particular adsorbent makes it possible to reduce the amount of adsorbent needed to separate the extract component contained in a particular charge rate of feed mixture. A reduction in the amount of adsorbent required for a specific adsorptive separation reduces the cost of the separation process. It is important that the good initial capacity of the adsorbent be maintained during actual use in the separation process over some economically desirable life.

The second necessary adsorbent characteristic is the ability of the adsorbent to separate components of the feed; or, in other words, that the adsorbent possess adsorptive selectivity, (B), for one component as compared to another component. Relative selectivity can be expressed not only for one feed component as compared to another but can also be expressed between any feed mixture component and the desorbent material. The selectivity, (B), as used throughout this specification is defined as the ratio of the two components of the adsorbed phase over the ratio of the same two components in the unadsorbed phase at equilibrium conditions.

Relative selectivity is shown as Equation 1 below:

$$\text{Selectivity} = (B) = \frac{[\text{vol. percent } C/\text{vol. percent } D]_A}{[\text{vol. percent } C/\text{vol. percent } D]_U} \quad \text{Equation 1}$$

where C and D are two components of the feed represented in volume percent and the subscripts A and U represent the adsorbed and unadsorbed phases respectively. The equilibrium conditions are determined when the feed passing over a bed of adsorbent does not change composition after contacting the bed of adsorbent. In other words, there is no net transfer of material occurring between the unadsorbed and adsorbed phases.

Where selectivity of two components approaches 1.0 there is no preferential adsorption of one component by the adsorbent with respect to the other; they are both adsorbed (or non-adsorbed) to about the same degree with respect to each other. As the (B) becomes less than or greater than 1.0 there is a preferential adsorption by the adsorbent for one component with respect to the other. When comparing the selectivity by the adsorbent of one component C over component D, a (B) larger than 1.0 indicates preferential adsorption of component C within the adsorbent. A (B) less than 1.0 would indicate that component D is preferentially adsorbed leaving an unadsorbed phase richer in component C and an adsorbed phase richer in component D. While separation of an extract component from a raffinate component is theoretically possible when the selectivity of the adsorbent for the extract component with respect to the raffinate component just exceeds a value of 1.0, it is preferred that such selectivity have a value approaching or exceeding 2. Like relative volatility, the higher the selectivity the easier the separation is to perform. Higher selectivities permit a smaller amount of adsorbent to be used in the process. Ideally desorbent materials should have a selectivity equal to about 1 or less than 1 with respect to all extract components so that all of the extract components can be extracted as a class and all raffinate components clearly rejected into the raffinate stream.

The third important characteristic is the rate of exchange of the extract component of the feed mixture material or, in other words, the relative rate of desorption of the extract component. This characteristic relates directly to the amount of desorbent material that must be employed in the process to recover the extract component from the adsorbent; faster rates of exchange reduce the amount of desorbent material needed to remove the extract component and therefore permit a reduction in the operating cost of the process. With faster rates of exchange, less desorbent material has to be pumped through the process and separated from the extract stream for reuse in the process.

In order to test various adsorbents and desorbent material with a particular feed mixture to measure the adsorbent characteristics of adsorptive capacity and selectivity and exchange rate, a dynamic testing apparatus is employed. The apparatus consists of an adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Chromatographic analysis equipment can be attached to the outlet line of the chamber and used to analyze "on-stream" the effluent stream leaving the adsorbent chamber.

A pulse test, performed using this apparatus and the following general procedure, is used to determine selectivities and other data for various adsorbent systems. The adsorbent is filled to equilibrium with a particular desorbent by passing the desorbent material through the adsorbent chamber. At a convenient time, a pulse of feed containing known concentrations of a non-adsorbed paraffinic tracer (n-nonane for instance) and of the particular aromatic isomers all diluted in desorbent is injected for a duration of several minutes. Desorbent flow is resumed, and the tracer and the aromatic isomers are eluted as in a liquid-solid chromatographic operation. The effluent can be analyzed by on-stream chromatographic equipment and traces of the envelopes of corresponding component peaks developed. Alternately, effluent samples can be collected periodically and later analyzed separately by gas chromatography.

From information derived from the chromatographic traces, adsorbent performance can be rated in terms of capacity index for an extract component, selectivity for one isomer with respect to the other, and the rate of desorption of an extract component by the desorbent. The capacity index may be characterized by the distance between the center of the peak envelope of the selectively adsorbed isomer and the peak envelope of the tracer component or some other known reference point. It is expressed in terms of the volume in cubic centimeters of desorbent pumped during this time interval. Selectivity, (B), for an extract component with respect to a raffinate component may be characterized by the ratio of the distance between the center of an extract component peak envelope and the tracer peak envelope (or other reference point) to the corresponding distance between the center of a raffinate component peak envelope and the tracer peak envelope. The rate of exchange of an extract component with the desorbent can generally be characterized by the width of the peak envelopes at half intensity. The narrower the peak width the faster the desorption rate. The desorption rate can also be characterized by the distance between the center of the tracer peak envelope and the disappearance of an extract component which has just been desorbed. This distance is again the volume of desorbent pumped during this time interval.

The adsorbent to be used in the process of this invention comprises a specific crystalline aluminosilicate. Crystalline aluminosilicates such as that encompassed by the present invention include crystalline aluminosilicate cage structures in which the alumina and silica tetrahedra are intimately connected in an open three-dimensional network. The tetrahedra are cross-linked by the sharing of oxygen atoms with spaces between the tetrahedra occupied by water molecules prior to partial or total dehydration of this zeolite. The dehydration of the zeolite results in crystals interlaced with cells having molecular dimensions. Thus, the crystalline aluminosilicates are often referred to as "molecular sieves" when the separation which they effect is dependent essentially upon differences between the sizes of the feed molecules as, for instance, when smaller normal paraffin molecules are separated from larger isoparaffin molecules by using a particular molecular sieve. In the process of this invention, however, the term "molecular sieves" although widely used is not strictly suitable since the separation of specific aromatic isomers is apparently dependent on differences in electrochemical attraction of the different isomers and the adsorbent rather than on pure physical size differences in the isomer molecules.

In hydrated form, the crystalline aluminosilicates generally encompass those zeolites represented by the Formula below:

$$M_{2/n}O:Al_2O_3:wSiO_2:yH_2O \qquad \text{Formula 1}$$

where "M" is a cation which balances the electrovalence of the tetrahedra and is generally referred to as an exchangeable cationic site, "n" represents the valence of the cation, "w" represents the moles of $SiO_2$, and "y" represents the moles of water. The generalized cation "M" may be monovalent, divalent or trivalent cations or mixtures thereof.

The prior art has generally recognized that adsorbents comprising the type X and the type Y zeolites can be used in certain adsorptive separation processes. These zeolites are well known to the art.

The type X structured zeolite in the hydrated or partially hydrated form can be represented in terms of mole oxides as shown in Formula 2 below:

$$(0.9\pm0.2)M_{2/n}O:Al_2O_3:(2.5\pm0.5)SiO_2:yH_2O \qquad \text{Formula 2}$$

where "M" represents at least one cation having a valence of not more than 3, "n" represents the valence of "M", and "y" is a value up to about 9 depending upon the identity of "M" and the degree of hydration of the crystal. As noted from Formula 2 the $SiO_2/Al_2O_3$ mole ratio is $2.5\pm0.5$. The cation "M" may be one or more of a number of cations such as the hydrogen cation, the alkali metal cation, or the alkaline earth cations, or other selected cations, and is generally referred to as an exchangeable cationic site. As the type X zeolite is initially prepared, the cation "M" is usually predominately sodium and the zeolite is therefore referred to as a sodium-type X zeolite. Depending upon the purity of the reactants used to make the zeolite, other cations mentioned above may be present, however, as impurities.

The type Y structured zeolite in the hydrated or partially hydrated form can be similarly represented in terms of mole oxides as in Formula 3 below:

$$(0.9\pm0.2)M_{2/n}O:Al_2O_3:wSiO_2:yH_2O \qquad \text{Formula 3}$$

where "M" is at least one cation having a valence not more than 3, "n" represents the valence of "M", "w" is a value greater than about 3 up to 6, and "y" is a value up to about 9 depending upon the identity of "M", and the degree of hydration of the crystal. The $SiO_2/Al_2O_3$ mole ratio for type Y structured zeolites can thus be from about 3 to about 6. Like the type X structured zeolite, the cation "M" may be one or more of a variety of cations but, as the type Y zeolite is initially prepared, the cation "M" is also usually predominately sodium. The type Y zeolite containing predominately sodium cations at the exchangeable cationic sites is therefore referred to as a sodium type-Y zeolite. It is only sodium or calcium type-Y or sodium type-X zeolites that may be used in the process of the present invention without amounts of other cations which would materially affect the characteristics of the adsorbent. This is in contradistinction to Rosenfeld et al. which requires a zeolite having a cesium and/or thallium content.

Typically, adsorbents used in separative processes contain the crystalline material dispersed in an amorphous material or inorganic matrix, having channels and cavities therein which enable liquid access to the crystalline. Silica, alumina, or mixtures thereof are typical of such inorganic matrix materials. The binder aids in forming or agglomerating the crystalline particles which otherwise would comprise a fine powder. The adsorbent may thus be in the form of particles such as extrudates, aggregates, tablets, macrospheres or granules having a desired particle range, preferably from about 16 to about 60 mesh (Standard U.S. Mesh). Less water content in the adsorbent is advantageous from the standpoint of less water contamination of the product.

The adsorbent may be employed in the form of a dense fixed bed which is alternatively contacted with a feed mixture and a desorbent material in which case the process will be only semicontinuous. In another embodiment, a set of two or more static beds of adsorbent may be employed with appropriate valving so that a feed mixture can be passed through one or more adsorbent beds of a set while a desorbent material can be passed through one or more of the other beds in a set. The flow of a feed mixture and a desorbent material may be either up or down through an adsorbent in such beds. Any of the conventional apparatus employed in static bed fluid-solid contacting may be used.

Moving bed or simulated moving bed flow systems, however, have a much greater separation efficiency than fixed bed systems and are therefore preferred. In the moving bed or simulated moving bed processes, the retention and displacement operations are continuously taking place which allows both continuous production of an extract and a raffinate stream and the continual use of feed and displacement fluid streams. One preferred embodiment of this process utilizes what is known in the art as the simulated moving bed countercurrent flow system. In such a system, it is the progressive movement of multiple liquid access points down a molecular sieve chamber that simulates the upward movement of molecular sieve contained in the chamber. Reference can also be made to D. B. Broughton's U.S. Pat. No. 2,985,589, in which the operating principles and sequence of such a flow system are described, and to a paper entitled, "Continuous Adsorptive Processing—A New Separation Technique" by D. B. Broughton presented at the 34th Annual Meeting of the Society of Chemical Engineers at Tokyo, Japan on Apr. 2, 1969, both references incorporated herein by reference, for further explanation of the simulated moving bed countercurrent process flow scheme.

Another embodiment of a simulated moving bed flow system suitable for use in the process of the present invention is the co-current high efficiency simulated moving bed process disclosed in U.S. Pat. No. 4,402,832 to Gerhold, incorporated by reference herein in its entirety.

It is contemplated that at least a portion of the extract output stream will pass into a separation means wherein at least a portion of the desorbent material can be separated at separating conditions to produce an extract product containing a reduced concentration of desorbent material. Preferably, but not necessary to the operation of the process, at least a portion of the raffinate output stream will also be passed to a separation means wherein at least a portion of the desorbent material can be separated at separating conditions to produce a desorbent stream which can be reused in the process and a raffinate product containing a reduced concentration of desorbent material. Typically the concentration of desorbent material in the extract product and the raffinate product will be less than about 5 vol.% and more preferably less than about 1 vol.%. The separation means will typically be a fractionation column, the design and operation of which is well known to the separation art.

Although both liquid and vapor phase operations can be used in many adsorptive separation processes, liquid-phase operation is preferred for this process because of the lower temperature requirements and because of the higher yields of an extract product that can be obtained with liquid-phase operation over those obtained with vapor-phase operation. Adsorption conditions will include a temperature range of from about 20° C. to about 250° C. with about 100° C. to about 200° C. being more preferred and a pressure sufficient to maintain liquid phase. Desorption conditions will include the same range of temperatures and pressure as used for adsorption conditions.

The size of the units which can utilize the process of this invention can vary anywhere from those of pilot-plant scale (see for example U.S. Pat. No. 3,706,812) to those of commercial scale and can range in flow rates from as little as a few cc an hour up to many thousands of gallons per hour.

The following examples are presented for illustration purposes and more specifically are presented to illustrate the selectivity relationships that make the process of the invention possible. Reference to specific cations, desorbent materials, feed mixtures and operating conditions is not intended to unduly restrict the scope and spirit of the claims attached hereto.

EXAMPLE I

In this experiment, three pulse tests were performed to evaluate the ability of the present invention to separate diethylbenzene isomers. The adsorbent used was a Y structured zeolite and a small portion of amorphous binder material. The zeolite as supplied by the manufacturer, contained sodium cations at substantially all exchangeable cationic sites. Two of the tests used one of the desorbents within the scope of the present invention and, for comparison purposes, in one test a desorbent outside such scope was used. The adsorbent was dried to essentially complete dryness before it was utilized in the process.

The testing apparatus was the above described pulse test apparatus. For each pulse test, the column was maintained at a temperature of 150° C. and a pressure of 100 psig to maintain liquid-phase operations. Gas chromatographic analysis equipment was attached to the column effluent stream in order to determine the composition of the effluent material at given time intervals. The feed mixture employed for each test contained about 5 vol.% each of the ethyltoluene isomers, 4 vol.% normal nonane which was used as a tracer and 81 vol.% desorbent material. The desorbent material in the first test was toluene (not in accordance with the present invention), in the second test ethylbenzene and in the third test m-xylene. In each test the desorbent comprised 30 vol.% of the aromatic material, with the remainder being n-$C_7$ paraffin. The operations taking place for each test were as follows. The desorbent material was run continuously at a nominal liquid hourly space velocity (LHSV) of 1.0 which amounted to about 1.17 cc per minute feed rate of desorbent. At some convenient time interval the desorbent was stopped and the feed mixture was run for a 10-minute interval at a rate of 1.0 cc per minute. The desorbent stream was then resumed at 1 LHSV and continued to pass into the adsorbent column until all of the feed aromatics had been eluted from the column as determined by observing the chromatograph generated by the effluent material leaving the adsorption column. The sequence of operations usually takes about an hour. The 10-minute pulse of feed and subsequent desorption may be repeated in sequence as often as is desired. Selectivities derived from the chromatographic traces are given in Table 1.

TABLE 1

| Desorbent: | Toluene | Ethylbenzene | m-Xylene |
|---|---|---|---|
| | 1.08 | 1.88 | 2.38 |
| | 0.80 | 2.05 | 2.38 |

$$\text{Selectivity} \begin{cases} \dfrac{\text{o-DEB}}{\text{p-DEB}} = \\ \dfrac{\text{o-DEB}}{\text{m-DEB}} = \end{cases}$$

It is clear from Table 1 that only the aromatic desorbents of at least $C_8$ weight when used with the sodium Y-type zeolite enable acceptable selectivities for the ortho-isomers.

EXAMPLE II

Pulse tests identical to those of Example I were run except that the feedstream comprised 5 vol.% of each isomer of ethyltoluene, 4 vol.% normal nonane and 81 vol.% desorbent material. The resuls obtained with various desorbent materials are set forth in Table 2. In this example, half widths and retention volumes are also given for further illustration.

TABLE 2

| | Ethyl-Benzene | Meta Xylene | Ortho Xylene | Para Xylene | P-DEB |
|---|---|---|---|---|---|
| Desorbent | | | | | |
| Half Widths cc | | | | | |
| n-Cg | 10.1 | 10.4 | 9.9 | 10.9 | 10.0 |
| p-EtTol | 14.6 | 14.2 | 19.3 | 18.2 | 20.1 |
| m-EtTol | 14.3 | 14.5 | 17.8 | 18.1 | 20.6 |
| o-EtTol | 16.6 | 13.8 | 11.2 | 11.7 | 36.7 |
| Retention Vol. cc | | | | | |
| p-EtTol | 23.1 | 4.4 | 10.9 | 10.0 | 17.3 |
| m-EtTol | 21.0 | 5.1 | 13.0 | 11.5 | 17.6 |
| o-EtTol | 38.2 | 9.2 | 20.9 | 24.1 | 63.6 |
| Selectivities | | | | | |
| o/p | 1.65 | 2.09 | 1.92 | 2.41 | 3.7 |
| o/m | 1.82 | 1.80 | 1.61 | 2.10 | 3.6 |

Again, it can be seen that in all embodiments of the present invention, the selectivities for ortho-ethyltoluene are satisfactory. The para-xylene is a particularly effective desorbent in view of the high selectivities and low retention volumes for the ortho-ethyltoluene, a combination which would ensure commercial applicability.

Further pulse tests employing ethylbenzene as a desorbent material over a temperature range from 125° C. to 175° C. indicated that the process temperature does not significantly affect the separation.

EXAMPLE III

Pulse tests identical to those of Example I were run except that sodium X or calcium Y-type zeolites were used with various desorbent materials. The results are as set forth in Table 3.

TABLE 3

| Adsorbent | Na-X | | | Ca-Y | | | |
|---|---|---|---|---|---|---|---|
| Wt. % H$_2$O Desorbent | ← Toluene | 0 Benzene | → Et Benz. | 0 Toluene | 0 p-xyl | 1.0 p-xyl | 1.0 Benzene |
| Half Widths, cc | | | | | | | |
| n-Cg | 10.0 | 6.0 | 8.1 | 12.7 | 13.6 | 10.7 | 10.2 |
| p-EtTol | 22.7 | 17.8 | 18.3 | 25.4 | 31.2 | 21.4 | 21.4 |
| m-EtTol | 18.7 | 14.9 | 15.0 | 21.4 | 31.5 | 18.1 | 19.5 |
| o-EtTol | 6.5 | 21.5 | 15.8 | 21.8 | 34.5 | 17.4 | 17.3 |
| Retention Vol., cc | | | | | | | |
| p-EtTol | 17.7 | 13.8 | 21.3 | 17.8 | 15.0 | 19.1 | 17.0 |
| m-EtTol | 23.0 | 20.0 | 26.0 | 23.0 | 18.4 | 23.3 | 21.5 |
| o-EtTol | 32.1 | 36.0 | 34.5 | 42.2 | 45.5 | 39.9 | 39.1 |
| Selectivities | | | | | | | |
| o/p | 1.8 | 2.6 | 1.6 | 2.4 | 3.0 | 2.1 | 2.3 |
| o/m | 1.4 | 1.8 | 1.3 | 1.8 | 2.5 | 1.7 | 1.8 |

It is again apparent that satisfactory selectivities for ortho-ethyltoluene are obtained for additional embodiments of the present invention, although the o/m selectivities for the Na-X/toluene and Na-X/ethylbenzene are close to the borderline for practical application.

It can also be seen from the data that when Ca-Y is employed, the water content thereof has an effect on selectivities. The optimum water content for that adsorbent is about 1.0 wt.%.

I claim as my invention:

1. A process for separating the ortho-isomer from a feed mixture comprising at least two bi-alkyl substituted mono-cyclic aromatic isomers, including the ortho-isomers, said isomers having from 9 to about 18 carbon atoms per molecule, which process comprises contacting, at adsorption conditions, said feed with an adsorbent comprising a crystalline aluminosilicate consisting essentially of a sodium Y-type zeolite which selectively adsorbs said ortho-isomer, removing said feed from said adsorbent, and recovering said ortho-isomer by desorption at desorption conditions with a desorbent material comprising a $C_8$ or heavier monocyclic aromatic, said feed mixture and said desorbent material having boiling points of at least 5° C. difference.

2. The process of claim 1 wherein said adsorption and desorption conditions include a temperature within the range of from about 20° C. to about 250° C. and a pressure sufficient to maintain liquid phase.

3. The process of claim 1 wherein said feedstock comprises the isomers of ethyltoluene and said desorbent comprises ethylbenzene or a xylene.

4. The process of claim 1 wherein said feedstock comprises the isomers of ethyltoluene and said desorbent comprises p-diethylbenzene.

5. The process of claim 1 wherein said process is effected with a simulated moving bed flow system.

6. The process of claim 5 wherein said simulated moving bed flow system is of the countercurrent type.

7. The process of claim 5 wherein said simulated moving bed flow system is of the co-current high efficiency type.

8. The process of claim 1 wherein said adsorbent includes an amorphous inorganic oxide matrix.

9. A process for separating the ortho-isomer from a feed mixture comprising at least two bi-alkyl substituted monocyclic aromatic isomers, including the ortho-isomer, said isomers having from 9 to about 18 carbon atoms per molecule, which process comprises contacting, at adsorption conditions, said feed with an adsorbent comprising a crystalline aluminosilicate consisting essentially of a sodium X or calcium Y-type zeolite which selectively adsorbs said ortho-isomer, removing said feed from said adsorbent, and recovering said ortho-isomer by desorption at desorption conditions with a desorbent material comprising a $C_8$ or lighter monocyclic aromatic.

10. The process of claim 9 wherein said adsorption and desorption conditions include a temperature within the range of from about 20° C. to about 250° C. and a pressure sufficient to maintain liquid phase.

11. The process of claim 9 wherein said feedstock comprises the isomers of ethyltoluene.

12. The process of claim 9 wherein said process is effected with a simulated moving bed flow system.

13. The process of claim 12 wherein said simulated moving bed flow system is of the countercurrent type.

14. The process of claim 12 wherein said simulated moving bed flow system is of the co-current high efficiency type.

15. The process of claim 9 wherein said adsorbent includes an amorphous inorganic oxide matrix.

16. The process of claim 9 wherein said adsorbent contains about 1 wt.% water.

* * * * *